United States Patent [19]

Grollier

[11] Patent Number: 4,900,326

[45] Date of Patent: Feb. 13, 1990

[54] DYE COMPOSITION FOR HUMAN KERATINOUS FIBRES IN THE FORM OF FOAM, BASED ON 5,6-DIHYDROXYINDOLE

[75] Inventor: Jean F. Grollier, Paris, France

[73] Assignee: L'Oreal, Paris, France

[21] Appl. No.: 62,687

[22] Filed: Jun. 16, 1987

[30] Foreign Application Priority Data

Jun. 16, 1986 [LU] Luxembourg .............................. 86474

[51] Int. Cl.$^4$ ............................................... A61K 7/13
[52] U.S. Cl. ........................................ 8/409; 8/423; 8/424; 424/47
[58] Field of Search ........................... 8/424, 409, 423; 424/47

[56] References Cited

U.S. PATENT DOCUMENTS

| | | | |
|---|---|---|---|
| 2,934,396 | 4/1960 | Charle et al. | 8/423 |
| 3,131,152 | 4/1964 | Klausner | 252/303 |
| 3,194,734 | 7/1965 | Seemuller et al. | 8/423 |
| 4,208,183 | 6/1980 | Grollier et al. | 8/409 |
| 4,240,450 | 12/1980 | Grollier et al. | 8/406 |
| 4,529,404 | 7/1985 | Feinland et al. | 8/424 |

*Primary Examiner*—Robert A. Wax
*Attorney, Agent, or Firm*—Cushman, Darby & Cushman

[57] ABSTRACT

Dye composition for human keratinous fibres, and for hair in particular, containing at least 5,6-dihydroxyindole and at least 0.1% by weight of a foam generator in a cosmetically acceptable aqueous medium, packaged under pressure in an aerosol device in the presence of a propellent agent, under such conditions as to form a dyeing foam having a density below or equal to 0.4 g/cm$^3$ from the said device.

19 Claims, No Drawings

DYE COMPOSITION FOR HUMAN KERATINOUS FIBRES IN THE FORM OF FOAM, BASED ON 5,6-DIHYDROXYINDOLE

The present invention relates to a new composition for dyeing human keratinuous fibers, and especially hair, with 5,6-dihydroyxindole and to the process making use of this composition.

It is well known that natural biosynthesis of eumelanins from tyrosine involves several steps. One of these consists of the formation of 5,6-dihydroxyindole which is oxidized to yield a pigment which is one of the principal constituents of eumelanin.

Many hair-dyeing processes making use of 5,6-dihydroxyindole or of some of its derivatives have already been proposed in the past.

Thus, according to French Pat. No. 1,166,172, a solution containing 5,6-dihydroxyindole with an oxidizing agent or an oxidation catalyst, if desired, is applied to hair. French Patent Application No. 2,536,993 also recommends a dyeing process in several stages separated by rinsings and consisting in applying, in one step, a solution of a metal solt at an alkaline pH and, in another step, a solution of 5,6-dihydroxyindone.

After rinsing or shampooing, these two steps may or may not be followed by the application of hydrogen peroxide in order to regulate the final shade by means of lightening.

The processes of the state of the art involve various disadvantages insofar as they result either in weak shades, or in the production of shades which are strong but require a long exposure time. Another disadvantage of these processes is the need to employ several steps or to store the composition in several separate containers, to be mixed before use.

The applicant has found that it was possible to dye hair in a single step with a composition containing 5,6-dihydroxyindole by packaging and storing the dye composition in a pressurized aerosol device, in the presence of a propellant agent and a foam generator under conditions such as to form a foam by expansion in free air.

Surprisingly, the applicant has found that the color strength of the dye, when dispensed in foam form from the aerosol device, is clearly superior to that of the same composition when presented in the conventional solution or emulsion form, employed hitherto for dyeing hair with 5,6-dihydroxyindole.

The behavior of 5,6-dihydroxyindole in a foam is particularly suprising in its specificity.

The dye dispensed in foam form from the aerosol device produces shades which do not change after permanent waving; furthermore, it stains the scalp to a lesser extent.

The dyeing power of 5,6-dihydroxyindole is remarkably well preserved on storage in a package of this kind. When dispensed in foam form from a pressurized aerosol device, the composition according to the invention makes is possible, furthermore, to obtain less selective dyeing and better cover on white hair. Its use is particularly convenient and rapid insofar as it is stored in a single package and is applied in a single step and as the foam generated under pressure is distributed very rapidly and uniformly over hair, dyeing it.

The subject of the present invention consists, therefore, of a dye composition for human keratinous fibers, and hair in particular, based on 5,6-dihydroxyindole and at least one foam generator, packaged under pressure in an aerosol device in the presence of a propellant agent, under such conditions as to form a dyeing foam after being dispensed from the aerosol device.

Another subject of the invention consists of the process for dyeing human keratinous fibers and in particular hair making use of the foam dispensed from the aerosol device.

Other subjects of the invention will become apparent from reading the description and the examples which follow.

The product according to the invention is essentially characterized in that it consists of a composition containing at least 5,6-dihydroxyindole and at least 0.1% by weight of a foam generator, in a cosmetically acceptable aqueous medium, which is packaged under pressure in an aerosol device in the presence of a propellant agent, so as to form a dyeing foam having a density below or equal to 0.4 g/cm$^3$, after being dispensed from the said device.

5,6-dihydroxyindole is present in the composition according to the invention in concentrations of between 0.1 and 5 % by weight, and preferably between 0.5 and 2 %, based on the total weight of the composition to be pressurized.

The name "foam generator" is given to a product, preferably a surface-active agent or a foaming polymer or a mixture of these, which, at 1% in water, permits the formation of a foam having a density below or equal to 0.4 g/cm$^3$.

The density is determined according to the following method:

the cosmetic mixture is packaged in a single-block, bullet-necked aluminium can (45 x 128) with a Precision P 73 valve without a dip tube, having an axial dispenser actuator for a conical collar (021550). The aerosol can is filled in proportions of 90 g of the cosmetic medium to be tested and 10 g of Freon F 114/F 12 propellant gas (43/57). The manipulation is performed 24 hours after the pressurization of the aerosols in a room conditioned at 20° C.±1°, the hardware and the sample being at the same temperature. A cylindrical cup is weighed empy (let its weight be P 1), and then immediately filled with the foam produced by the aerosol. Each aerosol can is shaken before use so as to emulsify the propellant gas.

To give a uniform distribution of the foam in the cup, the aerosols are used head down with a rotary and uniform motion.

As soon as the foam has expanded, it is immediately and rapidly levelled with a spatula and the cup is re-weighed (let its weight be P 2).

The foam density is determined according to the following formula:

$$\text{density at 20° C.} = \frac{P2 - P1}{V}$$

(V is the volume of the cup). Three determinations are carried out for each medium, the value taken being the mean value of these determinations (in g/cm$^3$).

The surface-active agent will be chosen from nonionic, anionic, cationic or amphoteric surfactants which are well known in the state of the art. These agents are employed in the composition according to the invention in proportions of between 0.1 and 55 % by weight, and preferably between 1 and 40% by weight, based on the total weight of the composition to be pressurized.

The foaming polymer may be an anionic, nonionic, amphoteric or cationic polymer or else a mixture of these, with a molecular weight of 500 to 3,000,000.

As cationic foaming polymers, there may be mentioned:

quaternized vinylpyrrolidone/dialkylaminoalkyl acrylate and methacrylate copolymers described more particularly in French Pat. No. 2,077,143 such as, for example, the products sold by General Aniline under the trade names "Gafquat 734 or 755", cellulose ether derivatives containing quaternary ammonium groups such as those described in French Pat. No. 1,492,597 such as, for example, the polymers sold by Union Carbide under the trade names: "JR or LR" among which there may be mentioned the polymers called "JR 125", "JR 400", "JR 30 M", "LR 400" and "LR 30 M", cellulose copolymers or cellulose derivatives grafted with a water-soluble quaternary ammonium group such as, for example, the products sold by National Starch under the trade names "Celquat L 200" and "Celquat H 100", and polyoxyethylnated polyamines such as those sold by Henkel under the trade name of "Polyquat H".

Anionic foaming polymers may be chosen more particularly from the following polymers:

uncrosslinked polymrs of acrylic or methacrylic cid or their salts, crotonic acid/vinyl acetate copolymers grafted onto polyalkylene glycols, such as the product sold by Hoechst under the trade name "Aristoflex A", polymers of maleic acid or anhydride with methacrylic acid or polymers of maleic anhydride and vinyl ether, such as the products marketed by GAF under the trade names "Gantrez ES or AN", and in particular the product sold under the trade name "Gantrez ES 425", and substitued or unsubstituted copolymers of acrylamide and unsaturated carboxylic acids such as the N-tert-butylacrylamide/Nhydroxyethylacrylamide/acrylic acid terpolymer described in French Pat. No. 2,432,528.

Among the nonionic foaming polymers capable of being employed according to the invention there may be mentioned the partially acetylated polyvinyl alcohols and, in particular, the product sold by Hoeschst under the trade name of "Mowiol 40.88" and their ethers, such as those sold by GAF under the trade names of "Gantrez M".

Among the amphoteric foaming polymers capable of being employed according to the invention there may be mentioned, by way of examples, the methacrylic copolymers of the betaine type such as the resin sold by Mitsubishi Petrochemical under the trade name "Amphoset" or else acrylic terpolymers such as the product sold by National Starch under the trade name "Amphomer".

The foaming polymers are present in the compositions according to the invention in proportions of between 0.1 and 5% by weight based on the total weight of the composition to be pressurized.

The cosmetically acceptable aqueous medium preferably has a pH of between 4 and 11, and more particularly between 5 and 9.5, and it is adjusted with alkalifying or acidifying agents usually employed in hair-dye compositions.

In any event, the aqueous cosmetic medium containing a foam generator should permit the formation of a foam having a density below or equal to 0.4 g/cm$^3$, determined as indicated above.

In addition to water, these compositions may also contain solvents which are acceptable from a cosmetic standpoint, in proportions which do not affect foam formation. As examples, there may be mentioned the lower $C_1$–$C_4$ alkanols such as ethanol, isopropanol and tert-butyl alcohol, ethylene glycol monomethyl, monoethyl or monobutyl ethers and ethylene glycol monoethyl ether acetate. These solvents are present in proportions which are preferably less than 50% by weight and more particularly less than 20%, based on the total weight of the composition to be pressurized.

The compositions to be pressurized may be thickened with thickening agents chosen from sodium alginate, gum arabic, guar or carob gum, heterobiopolymers such as xanthane gum, pectins, cellulose derivatives such as methyl cellulose, hydroxyethyl cellulose, hydroxypropyl methyl cellulose, hydroxypropyl cellulose, carboxymethyl cellulose, crosslinked acrylic acid derivatives having thickening properties or else inorganic thickening agents such as bentonite. These thickening agents are preferably employed in the compositions according to the invention in proportions of between 0.1 and 5% by weight, and in particular between 0.5 and 3% by weight, based on the total weight of the composition to be pressurized.

If desired, these compositions may contain a reducing agent in a small quantity, preferably less than 0.5%, chosen from thiol acids or ascorbic acid.

the compositions of the invention may contain other adjuvants usually employed in hair-dyeing compositions, such as penetrating agents, swelling agents, sequestering agents, film-forming agents, antioxidants, buffers, electrolytes, perfumes, and the like. It is understood that these various adjuvants must be employed in such proportions that they do not prevent foam formation after the pressurized product has been dispensed from the aerosol device.

The propellant agents employed together with the dyeing composition in the aerosol device are volatile hydrocarbons such as butane, isobutane, propane, and preferably butane, partially or completely fluorinated hydrocarbons such as the products sold by Du Pont de Nemours under the trade name of "Freon", and more particularly dichlorodifluoromethane (F12) and 1,2-dichloro-1,1,2,2-tetrafluoroethane, which are employed by themselves or mixed, for example in the form of a 40:60 to 80:20 mixture.

The pressurized aerosol devices are preferably single-container devices.

The dyeing foam, which forms another subject of the invention, is obtained after expansion, in air, of the pressurized composition defined above, and has a density below or equal to 0.4 g/cm$^3$.

The process for dyeing human keratinous fibers, and especially hair, consists in applying to the fibers the foam which is dispensed from the aerosol device. The fibers may or may not be rinsed after application of the dyeing foam. If they are rinsed, the composition which is applied in foam form is kept in contact for a period of 5 minutes to 30 minutes, depending on the required shade. According to an embodiment of the invention, a progressive dyeing, that is to say a dyeing in several stages may be performed by successive applications of the same composition.

The applicant has found that the presentation in the form of a foam makes application particularly easy and enables the dye composition to be well distributed.

The examples which follow are intended to illustrate the invention without, however, being limiting in nature.

| EXAMPLE 1 | |
| --- | --- |
| Ethylene glycol monoethyl ether | 10 g |

EXAMPLE 1 (continued)

| | |
|---|---|
| 5,6-Dihydroxyindole | 0.5 g |
| Mixture of cetostearyl alcohol and sodium lauryl sulphate sold by Henkel under the trade name of "Sinnowax SX" | 0.9 g |
| Polyethoxylated $C_{10}$–$C_{12}$ alcohol (3 moles of ethylene oxide) sold by Henkel under the trade name of "Mergital AL 309" | 1.3 g |
| Polyethoxylated $C_{10}$–$C_{12}$ alcohol (5 moles of ethylene oxide) sold by Henkel under the trade name of "Mergital AL 589" | 0.9 g |
| Oleocetyldimethylhydroxyethylammonium chloride | 2.3 g |
| Monoethanolamine q.s. pH: 8.7 | |
| Thioglycolic acid | 0.3 g |
| Water q.s. | 100 g |

This composition is packaged in a simple single-container aerosol.

| | |
|---|---|
| Above composition | 90 g |
| Propellant: Freons 12/114 | 10 g |
| (57/43) | |
| Total: | 100 g |

The foam is applied directly to the hair. The foam spreads quickly on being applied. It is left in place for 5 to 10 minutes, and is then rinsed off with water. On light-background hair 90% of which is white, repeated application produces a progressive dyeing of the white hair to a natural shade.

EXAMPLES 2–3

Example 1 is repeated:

by using 1 g of 5,6-dihydroxyindole instead of 0.5 g, to produce, on medium-background hair 90% of which is white, a progressive dyeing of the white hair to a natural shade;

by using 1.5 g of 5,6-dihydroxyindole instead of 0.5 g, to produce, by repeated application to darkbackground hair 90% of which is white, a progressive dyeing of the white hair to a natural shade.

TABLE I

| Composition | 4 | 5 | 6 | 7 | 8 | 9 |
|---|---|---|---|---|---|---|
| 5,6-Dihydroxyindole in g % | 0.5 | 0.5 | 0.5 | 0.5 | 0.5 | 0.5 |
| Sodium lauryl ether sulphate oxyethylenated with 2 moles of ethylene oxide, in g % AS | 3 | 3 | | | | |
| N,N—Diethylaminopolyoxyethyl copra carboxylate lactate with 4 moles of ethylene oxide | | | 3 | 3 | | |
| Triethanolamine $C_{12}$–$C_{14}$ alkyl sulphate, in g % AS | | | | | 3 | |
| Sodium laurylsarcosinate | | | | | | 3 |
| Ethyl alcohol g | 10 | 10 | 10 | 10 | 10 | 10 |
| Citric acid q.s. pH | 5.5 | | 5.5 | | | |
| 2-Amino-2-methyl-1-propanol q.s. pH | | 8.5 | | 8.5 | 8.5 | 8.5 |
| Water q.s. g | 100 | 100 | 100 | 100 | 100 | 100 |

TABLE II

| Composition | 10 | 11 | 12 | 13 | 14 | 15 |
|---|---|---|---|---|---|---|
| 5,6-Dihydroxyindole in g % | 0.5 | 0.5 | 0.5 | 0.5 | 0.5 | 0.5 |
| Ricinoleylmonoethanolamide disodium sulphosuccinate | 3 | | | | | |
| Sodium Laureth-13 carboxylate | | 3 | | | | |
| Oleocetyldimethylhydroxyethylammonium chloride | | | 3 | | | |
| Octylphenol with 10 moles of ethylene oxide | | | | 3 | | |
| $R-\underset{\underset{O}{\|\|}}{C}-NH-CH_2-CH_2-\underset{\underset{CH_2COONa}{\|}}{\overset{\overset{CH_2-CH_2OH}{\|}}{N^{\oplus}}}-CH_2COO^{\ominus}$ $R-\underset{\underset{O}{\|\|}}{C}$ = Copra fatty acid radical | | | | | 3 | |
| Dodecanediol polyglycerolated with 3.5 moles | | | | | | 3 |
| Ethyl alcohol in g | 10 | 10 | 10 | 10 | 10 | 10 |
| 2-Amino-2-methyl-1-propanol q.s. pH | 8.5 | 8.5 | 8.5 | 8.5 | 8.5 | 8.5 |
| Water q.s. g | 100 | 100 | 100 | 100 | 100 | 100 |

EXAMPLE 16

| EXAMPLE 16 | |
|---|---|
| 5,6-Dihydroxyindole | 1 g |
| Hydroxyethyl cellulose copolymer grafted with diallyldimethylammonium chloride, sold by National Starch under the trade name of "Celquat L 200" | 0.8 g AS |
| pH: 5.7 natural | |
| Water q.s. | 100 g |

EXAMPLE 17

| EXAMPLE 17 | |
|---|---|
| 5,6-Dihydroxyindole | 1.5 g |
| (Tallow)alkyltrimethylammonium chloride sold as a mixture with isopropyl alcohol at a concentration of 50% by Armak under the | |

-continued

EXAMPLE 17

| | |
|---|---|
| trade name "Arquad T 50" | 1 g AS |
| Hydroxyethyl cellulose/epichlorohydrin polymer quaternized with trimethylamine, sold by Union Carbide under the trade name "JR 400" | 0.5 g |
| pH: 5.3 natural | |
| Water q.s. | 100 g |

The compositions of Tables I and II and those of Examples 16 and 17 are packaged in a simple single-container aerosol device.

| | |
|---|---|
| Above composition (4 to 15) | 90 g |
| Freon 12/114 (57/43) | 10 g |
| Total | 100 g |

The foam is applied to the hair in a similar manner to that in Example 1. After several applications, the white hair takes up a natural color.

EXAMPLE 18

| EXAMPLE 18 | |
|---|---|
| 5,6-Dihydroxyindole | 2 g |
| Isopropyl alcohol | 5 g |
| Sodium laureth-13 carboxylate | 2 g |
| Sodium laurylsarcosinate | 2 g |
| Water q.s. | 100 g |
| Natural pH: 7 | |
| Aerosol packaging: | |
| Above composition: | 90 g |
| Freon 12/114 (57/43): | 10 g |
| Total | 100 g |

The foam is applied to 90% white natural hair. It is left in place for 10 min and is rinsed off with water.

After one application the hair is dyed a natural grey shade.

EXAMPLE 19

| EXAMPLE 19 | |
|---|---|
| 5,6-Dihydroxyindole | 0.8 g |
| Ethylene glycol monoethyl ether | 4 g |
| Xanthan gum sold by Rhone-Poulenc under the trade name Rhodopol SC. | 0.5 g |
| Nonionic surfactant produced according to French Patent 71/17,206 by the condensation of 3.5 moles of glycidol with a $C_{11}$-$C_{14}$ α-diol | 1 g |
| Triethanolamine q.s. pH: 7 | |
| Water q.s. | 100 g |
| Aerosol packaging: | |
| Above composition: | 90 g |
| Freon 12/114 (57/43): | 10 g |
| Total | 100 g |

The foam is applied to 90% white natural hair. After one application which is not followed by rinsing, the hair is hyed a natural grey shade.

EXAMPLE 20

The foam is applied to 90% while natural hair. It is left in place for 10 min. It is rinsed off with water. After 3 successive applications the hair is dyed a natural medium grey shade.

I claim:

1. A dye composition for human keratinous fibers comprising at least 5,6-dihydroxyindole present in an amount effective to dye said human keratinous fibers and at least 0.1 percent by weight of a foam generator in a cosmetically acceptable aqueous medium, said composition being packaged, under pressure, in an aerosol device in the presence of a propellant agent, under such conditions so as to form a dyeing foam having a density below or equal to 0.4 g/cm$^3$ when dispensed from said aerosol device.

2. The dye composition of claim 1 wherein said 5,6-dihydroxyindole is present in an amount ranging from 0.1 to 5 percent by weight based on the total weight of the composition to be pressurized.

3. The dye composition of claim 1 wherein said 5,6-dihydroxyindole is present in the amount ranging from 0.5 to 2 percent by weight based on the total weight of the composition to be pressurized.

4. The dye composition of claim 1 wherein said foam generator is an anionic, nonionic, amphoteric or cationic surface-active agent, or a mixture thereof.

5. The dye composition of claim 4 wherein said surface-active agent is present in an amount ranging from 0.1 to 55 percent by weight based on the total weight of the composition to be pressurized.

6. The dye composition of claim 4 wherein said surfaceactive agent is present in an amount ranging from 1 to 40 percent by weight based on the total weight of the composition to be pressurized.

7. The dye composition of claim 1 wherein said foam generator is an anionic, cationic, nonionic or amphoteric foaming polymer.

8. The dye composition of claim 7 wherein said foaming polymer is selected from the group consisting of:
   (1) a quaternized vinylpyrrolidone/dialkylaminoalkyl acryhlate and methacrylate copolymer, cellulose ether derivative containing quaternary ammonium group, cellulose copolymer or cellulse derivative grafted with a water-soluble quaternary ammonium group, and apolyoxyethylenated polyamine;
   (2) an uncrosslinked polymer of acrylic or methacrylic acid or a solt thereof, crotonic acid/vinyl acetate copolymer grafted onto polyalkylene glycol, polymer of maleic acid or anhydride with methacrylic acid, polymer of maleic acid or anhydride ether, and substituted or unsubstituted copolymer of acrylamide and unsaturated carboxylic acid;
   (3) methacrylic copolymer in betaine form or amphoteric acrylic terpolymer; and
   (4) partially acetylated polyvinyl alcohol and polyvinyl alcohol ether.

9. The dye composition of claim 7 wherein said foaming polymer is present in an amount ranging from 0.1 to 5 percent by weight based on the total weight of the composition to be pressurized.

10. The dye composition of claim 1 wherein said aqueous medium has a pH ranging from 4 to 11.

11. The dye composition of claim 1 wherein said aqueous medium has a pH ranging from 5 to 9.5.

12. The dye composition of claim 1 wherein said aqueous medium contains a cosmetically acceptable organic solvent selected from the group consisting of a lower $C_1$-$C_4$ alkanol, ethylene glycol monomethyl ether, ethylene glycol monoethyl ether, ethylene glycol monobutyl ether and ethylene glycol monoethyl ether acetate, said solvent being present in an amount less than 50 weight percent based on the total weight of the composition to be pressurized.

13. The dye composition of claim 12 wherein said organic solvent is present in an amount less than 20 percent by weight based on the total weight of the composition to be pressurized.

14. The dye composition of claim 1 which also includes a thickening agent in an amount ranging from 0.1 to 5 percent by weight based on the total weight of the composition to be pressurized.

15. The dye composition of claim 1 wherein said propellant agent is a volatile hydrocarbon selected from the group consisting of butane, isobutane, propane, partially fluorinated hydrocarbon, completely fluorinated hydrocarbon and a mixture thereof.

16. Dyeing foam produced by dispensing said dye composition of claim 1 under pressure from an aerosol device, said dyeing foam having a density below or equal to 0.4 g/cm$^3$.

17. A process for dyeing human keratinous fibes comprising applying to said fibers the dyeing foam of claim 16, said foam being dispensed from an aerosol device.

18. A process for dyeing human keratinous fibers comprising applying to said fibers the dyeing foam of claim 16, said foam being dispensed from an aerosol device, permitting said foam to remain in contact with said fibers for a period of time ranging from 5 to 30 minutes and rinsing said fibers.

19. The process of claim 18 wherein said dyeing foam is applied to said fibers several times in succession.

* * * * *